United States Patent
Bova et al.

(10) Patent No.: US 7,697,969 B2
(45) Date of Patent: Apr. 13, 2010

(54) PREPLANNING OF GUIDED MEDICAL PROCEDURES

(75) Inventors: Frank Joseph Bova, Gainesville, FL (US); William Alan Friedman, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 635 days.

(21) Appl. No.: 11/545,752

(22) Filed: Oct. 10, 2006

(65) Prior Publication Data

US 2007/0100224 A1    May 3, 2007

Related U.S. Application Data

(60) Provisional application No. 60/726,083, filed on Oct. 11, 2005.

(51) Int. Cl.
*A61B 5/05* (2006.01)
*G06K 9/00* (2006.01)
*A61N 5/10* (2006.01)

(52) U.S. Cl. .................. 600/407; 600/414; 600/426; 600/427; 382/128; 382/294; 378/65

(58) Field of Classification Search .............. 600/407, 600/427, 562, 414, 426; 382/128, 294; 378/65
See application file for complete search history.

(56) References Cited

U.S. PATENT DOCUMENTS

| | | | |
|---|---|---|---|
| 5,207,223 A | 5/1993 | Adler et al. | |
| 5,373,844 A | 12/1994 | Smith et al. | |
| 5,899,861 A * | 5/1999 | Friemel et al. | 600/443 |
| 6,144,875 A * | 11/2000 | Schweikard et al. | 600/427 |
| 6,390,982 B1 * | 5/2002 | Bova et al. | 600/443 |
| 6,661,872 B2 * | 12/2003 | Bova | 378/65 |
| 6,778,850 B1 | 8/2004 | Adler et al. | |
| 2004/0092815 A1 | 5/2004 | Schweikard et al. | |
| 2004/0165696 A1 | 8/2004 | Lee | |

* cited by examiner

*Primary Examiner*—Eric F Winakur
*Assistant Examiner*—Katherine L Fernandez
(74) *Attorney, Agent, or Firm*—Thomas, Kayden, Horstemeyer & Risley, LLP

(57) ABSTRACT

A method of preplanning for guided medical procedures includes obtaining a first 3D diagnostic dataset for a region of interest of a subject. This first dataset can be a non-stereotactic dataset and provide sufficient contrast to identify target tissue in the region of interest. A treatment preplan is developed to treat the target tissue using the first dataset exclusive of stereotactic data. The treatment preplan includes placement locations for a plurality of initial radiation beams and their respective dose intensities. A second, stereotactic 3D dataset can be obtained for the region of interest. A registered dataset can then be created by registering the first dataset to the second dataset. The treatment preplan can be modified using data associated with the registering step to generate a stereotactic treatment plan including a plurality of radiation treatment beams with respective placement positions based on the registered dataset to treat the target tissue.

10 Claims, 1 Drawing Sheet

PREPLANNING OF GUIDED MEDICAL PROCEDURES

CROSS REFERENCE TO RELATED APPLICATIONS

This application claims the benefit of U.S. Provisional Patent Application Ser. No. 60/726,083, filed on Oct. 11, 2005, entitled "PREPLANNING OF GUIDED MEDICAL PROCEDURES", the entirety of which is incorporated herein by reference.

STATEMENT REGARDING FEDERALLY SPONSORED RESEARCH OR DEVELOPMENT

Not applicable.

FIELD OF THE INVENTION

This invention relates generally to the fields of medicine, radiology and neurosurgery. More particularly, the invention relates to methods for image-guided medical procedures, such as radiosurgery, radiotherapy or biopsy.

BACKGROUND

Many modern medical procedures, both invasive and non-invasive, are performed with the assistance of medical imaging devices. A series of two-dimensional images generated from devices such as computed tomography (CT) or magnetic resonance (MR) scanners are used to generate virtual 3-dimensional models of regions of interest from subjects. These models are used in the planning, practice and execution of medical procedures subsequently performed on the patients. Image-guided medical procedures are generally accomplished by coordinating 3-D virtual models of subjects with reference points on the actual subjects undergoing the medical procedures.

Current approaches for image-guided medical procedures such as stereotactic biopsy or radiation therapy can be divided into two stereotactic approaches. Stereotactic is defined herein and is generally defined as a method utilizing 3-dimensional mapping to precisely locate areas in space suitable for guidance in medical procedures. Historically, stereotactic approaches have been used for procedures on areas of the brain and more recently for procedures in extra-cranial regions. The first approach uses a rigid frame secured to the subject, such as a human patient. The second approach is a frameless approach, in which fiducial landmarks, either derived from the patient's own anatomical features or applied to a surface of the patient, are used to coordinate the 3-D virtual patient model to the real world patient.

In the rigid frame approach, a stereotactic frame is rigidly attached to the patient by placing fasteners directly to the skull. A detailed 3-D image map is then created from CT, MR, or other 3-D imaging source. Fiducial markers placed on the stereotactic frame appear in the images and allow objects in the image to be related to the stereotactic frame. Hence, targets of interest, such as a tumor and its surrounding anatomy, can be described using the coordinates of the stereotactic frame as a reference. The patient is then transferred to the operating room for treatment with the stereotactic frame remaining in place, thus again using the stereotactic frame as a reference. Although this approach eliminates the error-generating step of registering the virtual model to the actual subject, this approach is invasive and results in discomfort for the patients.

In the frameless approach, the registration of the patient to the image-based operative model requires the identification of fiducial markers. Some fiducials are external markers applied to the patient prior to scanning and are kept in place until registration has been completed, while other reference markers are actually identifiable anatomic landmarks based on the patient's own anatomy. The identification of these fiducial points can be difficult and can add significant time to the operative procedure. Additionally, movement of the fiducials relative to internal anatomy can degrade the accuracy of the registration process and subsequently detract from the overall accuracy of the image-guided procedure.

Another method of obtaining a data set for stereotactic guidance is to provide a method of automatically mapping an image data set to a volume by defining the scan volume. In the case of large fixed equipment, such as a medical linear accelerator, the volume scanned by the imaging device can be mapped to a fixed point in the room. This is similar to the stereotactic mapping that is performed in carrying out procedures for ultrasonic guidance for the application of therapeutic radiation treatments. Alternatively, a reference can be applied to the scanning equipment and a second reference on the patient allowing the patient and the scanned data to be mapped to one another.

For non-spherically shaped tumors, as most tumors are, physicians generally attempt to fill the target with several radiation spheres of different sizes. This is referred to as a "sphere packing" treatment plan. Such methods require many computations in order to compute a radiosurgical plan dose distribution, and then require evaluation of the quality of the dose distribution.

In most systems a stereotactic ring apparatus or fiducial markers are applied to the patient to generate the images and then the planning process is initiated within minutes. However, planning might take two hours or more for a difficult case requiring about 15 to 20 spheres. During that time, the patient has to wait with the head ring attached to his or her head, or have fiducial markers remain disposed on his or her head. This places great restraints on the time necessary to derive an optimal plan as well as making expert consultation prohibitive.

SUMMARY OF THE INVENTION

The present invention provides for a method of preplanning guided medical procedures that includes obtaining a first 3D diagnostic dataset for a region of interest of a subject. The first dataset can be a non-stereotactic dataset and can provide sufficient contrast to identify target tissue in said region of interest. A treatment preplan can be developed to treat or remove the target tissue based on the first dataset exclusive of any stereotactic data. The treatment preplan can include placement locations for a plurality of initial radiation beams and their respective dose intensities. A second, stereotactic 3D dataset for said region of interest can be obtained. The first dataset can be registered to the second dataset to create a registered dataset. The treatment preplan can be modified using data associated with the registering step to generate a stereotactic treatment plan including a plurality of radiation treatment beams having respective placement positions based on the registered dataset to treat or remove the target tissue.

In another embodiment, the modifying step can include adjusting the respective placement positions and relative intensities of the plurality of radiation treatment beams so that the dose delivered to the target tissue is substantially equal to the relative intensities of the plurality of initial radiation beams in said preplan. The developing step can include sphere packing.

In one embodiment, the second dataset can be derived using a stereotactic ring. The second dataset can be derived using a set of fiducials used to define an image space. In another embodiment, the second dataset can be derived from scanning the subject at a treatment site where the target tissue can be treated or removed using a conventional computed tomography (CT) scanner, a cone beam CT scanner or an in-room magnetic resonance (MR) scanner.

In another embodiment, the first dataset is derived from registered multiple non-stereotactic datasets.

In one embodiment, the registered dataset can include a transformation matrix for mapping the first dataset into the second dataset. The transformation matrix can transfer the preplan from the first dataset into the treatment plan based on the second dataset. In another embodiment, the transformation matrix can define a shift from a coordinate system associated with the first dataset to a stereotactic coordinate system associated with the second dataset.

In another embodiment, the method can also include performing radiosurgery or radiotherapy to treat the target tissue using the stereotactic treatment plan. The method can also include performing a biopsy on said target tissue using said stereotactic treatment plan.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
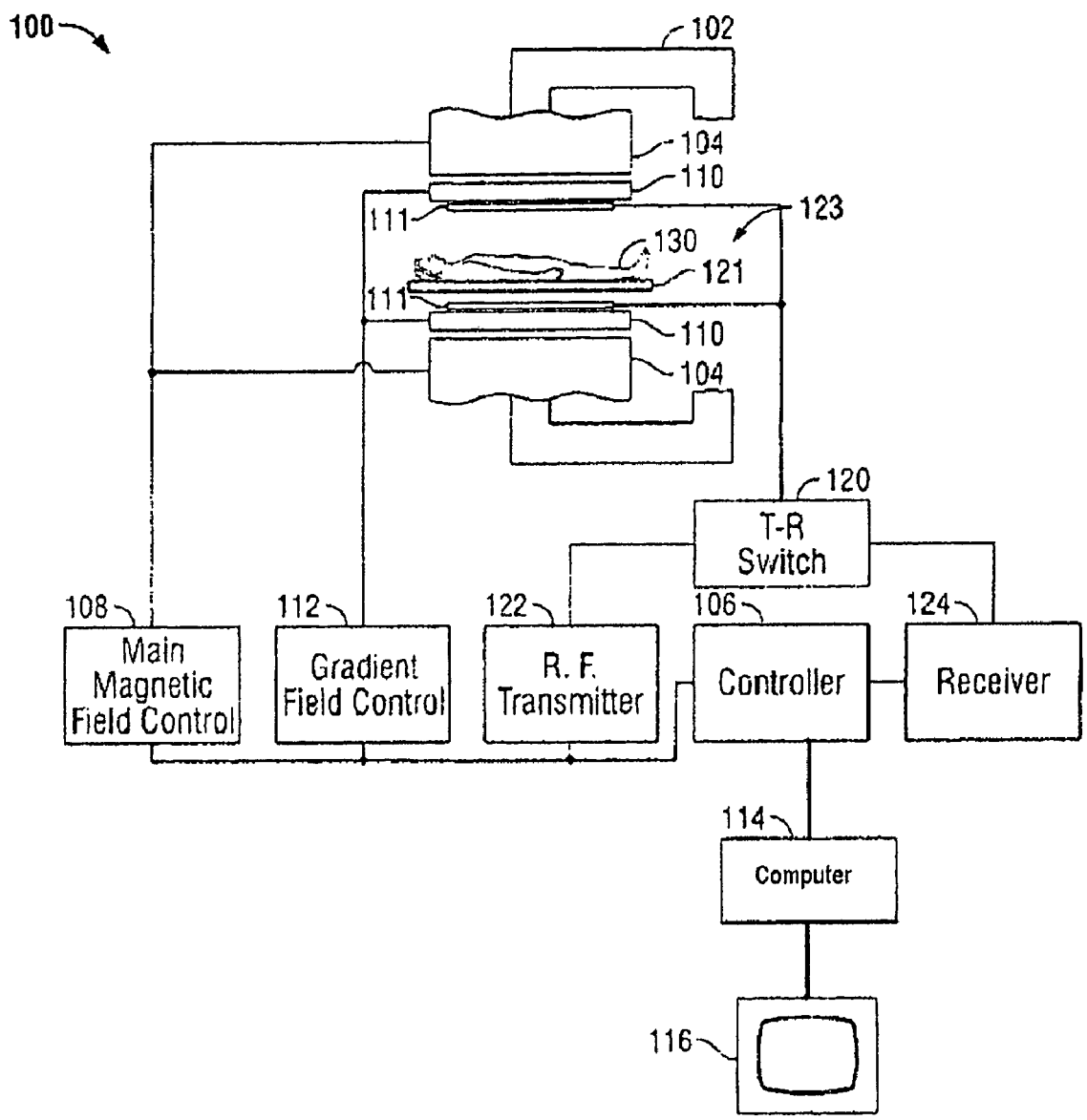
FIG. 1 shows a block diagram of an exemplary magnetic resonance (MR) system that may be used for obtaining 3D datasets for use with the present invention.

A method of preplanning for guided medical procedures comprises the steps of obtaining a first 3D diagnostic dataset for a region of interest of a subject, the first dataset being a non-stereotactic dataset. The first dataset provides sufficient contrast to identify target tissue in said region of interest. A treatment preplan to treat or remove the target tissue is then developed based on the first dataset exclusive of any stereotactic data. The treatment preplan includes placement locations for a plurality of initial radiation beams and their respective dose intensities. A second 3D dataset is then obtained for the region of interest. The second dataset is a stereotactic dataset. The first dataset is then registered to the second dataset. The treatment preplan is then modified using data associated with the registering step to generate a stereotactic treatment plan comprising a plurality of radiation treatment beams having respective placement positions based on the second dataset to treat or remove the target tissue.

A variety of imaging systems may be used to obtain 3D datasets useful in the present invention. A block diagram of one such imaging system, a magnetic resonance (MR) device 100, is shown in FIG. 1. As shown, the MR device 100 can include an electromagnet 102, pole pieces 104, a controller 106, a main magnetic field control 108, a gradient coil subsystem 110, a gradient field control 112, a transmit-receive (T-R) switch 120, a radio frequency (RF) transmitter 122, a receiver 124 and an array of detectors 111. In order to image a region of interest 130, the region of interest 130 can be placed in an opening 123 between the pole pieces 104 on a suitable support 121. The magnetic resonance device 100 can be communicably connected to a computer 114, which has a display device 116 connected thereto. The computer can be used to generate 3D datasets and 3D models from a series of two-dimensional images obtained using the MR device 100. The display device 116 can be used to view images. As noted above, and as will be recognized by one skilled in the art, this figure is illustrative of but one device useful in the present invention and that there are many other devices, including other MR scanners, computed tomography (CT) scanners, and the like, that may be used to obtain 3D datasets useful in the present invention.

The invention thus provides treatment planning before stereotactic data acquisition, and is generally referred to herein as "preplanning". For example, the invention applies to preplanning generally and can be used for preplanning for performing biopsies or preplanning of radiation treatment for radiosurgery or radiotherapy.

The inventive methodology allows such preplanning to occur on a first non-stereotactic medical dataset. That first dataset can, at some later time, be registered to a second data set which is associated with conventional stereotactic coordinates to generate a final treatment plan to be used for the actual radiography procedure.

There are significant advantages to being able to plan radiography procedures prior to the application of either the stereotactic ring system or the stereotactic fiducial. Because of the discomfort of the stereotactic frame and the potential of frame slippage or stereotactic fiducial movement, treatment usually follows within several hours of frame placement. Thus, it is usually considered unacceptable for days or weeks to lapse. The constraint of needing to treat the same day as image acquisition and not allowing days to a few weeks to elapse is often related to these comfort or slippage factors, not target growth, especially when benign targets are being considered. The preplanning capabilities of the present invention allow for improved planning and expert consultation.

There are other advantages of preplanning according to the invention. The advantages include the ability to understand the complexity of the final treatment plan and more appropriately schedule the procedure in order to minimize the time of ring application or to allow for remote planning or expert consultation (e.g. second opinions).

Tissue regions of interest of a patient or other subject are first imaged by obtaining a 3D preplanning image dataset. This can be diagnostic medical exam obtained through conventional MR or CT scanning, for example, an MR device similar to that shown in FIG. 1. The images obtained from the diagnostic exam allow the target tissues, as well as normal tissues, to be identified. An arbitrary coordinate system can be applied to the image dataset. This first dataset is not a stereotactic dataset in that no external fiducial or other markers are used in its generation. Thus, the dataset need not be capable of precisely locating areas in space suitable for guidance in medical procedures. The only general requirement for the initial dataset is that it is compatible with a subsequent image registration procedure.

A variety of coordinate systems can be used. In one embodiment of the invention, data set 1 is a rigid data set and data set 2 is a data set that provides registration. In another embodiment, data set 1 is a non-rigid data set and data set 2 provides alignment.

The inventive method preferably uses sphere packing and variants thereof as the radiosurgery planning technique. However, methods other than sphere packing, such as intensity modulated radiation therapy (IMRT), can be used with the invention to fill the target volume. For surgery, any available target trajectory can be used.

If sphere packing sets of non-coplanar radiation beams are applied to the target tissues, the target coordinate is termed an isocenter. Each beam set creates a spherical dose distribution. The packing process involves filling the target volume with multiple spheres of dose. Each sphere is assigned an appropriate intensity and placed at an appropriate spacing or location until the entire target structure is covered by appropriate dose profiles. The final plan is described by the listing of a set of spherical dose profiles at specific locations, isocenters, and with specific relative intensities. The locations of each sphere are defined using the coordinate system applied to the preplan image dataset.

The next step includes obtaining a second dataset, which can be obtained some time later, such as days or even weeks after the first 3D data set and preplan are determined. Generally, the only requirement is that the time following first data set acquisition be short enough so that changes in target growth or shape be insignificant. At this later time a second dataset is obtained. This second dataset is preferably a stereotactic dataset or a dataset capable of providing guidance.

In one embodiment a preplan including initial alignment is generated based on a non-stereotactic data set. The position of the treatment is not the same as the initial alignment. The plan is then adjusted to match a new orientation relative to the treatment equipment.

In a preferred embodiment, the second dataset will usually require the placement of a conventional head ring to the patient or the placement of fiducial (e.g. optical) markers on the patient. This second dataset is mapped to the defined stereotactic space. A registered dataset is the created by registering (mapping) the first dataset to the second dataset. This process preferably transfers each voxel of the first dataset to the location of the corresponding voxel of the second dataset, such as using rigid or non-rigid fusion, thus mapping the first image dataset into the second image's defined stereotactic space. The second dataset may also be taken by a device capable of imaging the patient after the patient has been positioned for the medical procedure. Such dataset can be obtained from in-room conventional CT scanners, cone beam CT scanners or in room MR scanners. When these devices are used, the patient is generally required to be immobilized or have a trackable reference fixed to the patient or to his or her immobilization device.

This mapping can be accomplished by deriving a transformation matrix that describes the shift from the coordinate system of the first image to the stereotactic coordinate system of the second image, such as using an affine transformation. Affine transformations are described on pages 30-33 in a book entitled "The Mathematical Structure of Raster Graphics", by Eugene L. Fine, these pages being incorporated by reference into this application.

The transformation matrix can also be used to transfer the specific location of the preplanned spheres (or other units) of dose to the stereotactic image dataset. A set of rules is then preferably used to ensure that the proper spacing and relative dose weighting have been maintained to deliver a dose to the target tissue that is substantially equal to that developed in the preplan. As used herein, "substantially equal" indicates the dose, i.e. the target prescription isodose surface, delivered after the transformation deviates from the preplan isodose by less than 50% or 3 mm or, more preferably, the dose delivered after the transformation deviates from the preplan isodose by less than 25% or 2 mm.

At a minimum, the inventive process requires appropriate software to be implemented and can be run on existing electronics provided by conventional radiosurgery systems, for instance, the computer 114 shown in FIG. 1. The invention can also be implemented for newly designed radiosurgery and radiotherapy planning systems.

A non-limiting prophetic example is provided below to demonstrate practice of the invention. A specific intracranial target may require two spheres, one being 20 mm diameter and one being 10 mm diameter spaced 18 mm from center to center with the ratio of dose for the larger sphere to smaller sphere being 1:0.75 to allow full coverage of the target tissues. The initial set of images can provide the information as to size, spacing and relative intensity. Once the first dataset is matched to the stereotactic dataset the required position of the spheres in stereotactic space can be derived from the matrix that mapped the position of the voxels at the spheres center, in non-stereotactic space were set.

This invention has been described herein in considerable detail to provide those skilled in the art with information relevant to apply the novel principles and to constrict and use such specialized components as are required. However, it is to be understood that the invention can be carried out by different equipment, materials and devices, and that various modifications, both as to the equipment and operating procedures, can be accomplished without departing from the scope of the invention itself.

What is claimed is:

1. A method of preplanning for guided medical procedures, comprising the steps of:
   obtaining a first 3D diagnostic dataset for a region of interest of a subject, said first dataset being a non-stereotactic dataset, said first dataset providing sufficient contrast to identify target tissue in said region of interest;
   developing a treatment preplan to treat or remove said target tissue based on said first dataset exclusive of any stereotactic data, said treatment preplan including placement locations for a plurality of initial radiation beams and their respective dose intensities;
   obtaining a second 3D dataset for said region of interest, said second dataset being a stereotactic dataset;
   registering said first dataset to said second dataset, wherein a registered dataset, comprising a transformation matrix for mapping said first dataset into said second dataset, is created, and
   transforming said treatment preplan using said transformation matrix for transferring said preplan from said first dataset into a treatment plan based on said second dataset to generate a stereotactic treatment plan comprising a plurality of radiation treatment beams delivering said respective dose intensities and having respective placement positions based on said registered dataset to treat or remove said target tissue.

2. The method of claim 1, wherein said transforming step includes adjusting said respective placement positions and relative intensities of said plurality of radiation treatment beams so that the dose delivered to the target tissue is substantially equal to said relative intensities of said plurality of initial radiation beams in said preplan.

3. The method of claim 1, wherein said developing step comprises sphere packing.

4. The method of claim 1, wherein said second dataset is derived using a stereotactic ring.

5. The method of claim 1, wherein said second dataset is derived using a set of fiducials used to define an image space.

6. The method of claim 1, wherein said second dataset is derived from scanning of said subject at a treatment site where said target tissue is treated or removed using a conventional CT scanner, a cone beam CT scanner or an in-room MR scanner.

7. The method of claim 1, wherein said first dataset is derived from registered multiple non-stereotactic datasets.

8. The method of claim 1, wherein said transformation matrix defines a shift from a coordinate system associated with said first dataset to a stereotactic coordinate system associated with said second dataset.

9. The method of claim 1, further comprising the step of, performing radiosurgery or radiotherapy to treat said target tissue using said stereotactic treatment plan.

10. The method of claim 1, further comprising the step of, performing a biopsy on said target tissue using said stereotactic treatment plan.

* * * * *